United States Patent [19]

Pelok

[11] Patent Number: 5,732,721
[45] Date of Patent: Mar. 31, 1998

[54] DENTAL FLOSS WITH A PRESSURE SENSITIVE MATERIAL

[76] Inventor: Brett S. Pelok, 6411 Coopersmith, Sylvania, Ohio 43560

[21] Appl. No.: 731,853

[22] Filed: Oct. 21, 1996

[51] Int. Cl.$^6$ ..................................... A61C 15/04
[52] U.S. Cl. ............................. 132/321; 428/372
[58] Field of Search ..................... 132/321, 329; 428/372, 364, 375, 398, 399; 433/71, 215

[56] References Cited

U.S. PATENT DOCUMENTS

| | | |
|---|---|---|
| 328,004 | 10/1885 | Church . |
| 2,299,693 | 10/1942 | Green . |
| 3,838,702 | 10/1974 | Standish et al. ............... 132/321 |
| 3,918,160 | 11/1975 | Friedman . |
| 3,942,539 | 3/1976 | Corliss et al. ............... 132/321 |
| 4,055,897 | 11/1977 | Brix . |
| 4,215,478 | 8/1980 | Thomas et al. . |
| 4,690,642 | 9/1987 | Kyotani . |
| 4,786,254 | 11/1988 | Millstein et al. . |
| 4,941,487 | 7/1990 | VanBeneden . |
| 4,986,288 | 1/1991 | Kent et al. . |
| 5,033,488 | 7/1991 | Curtis et al. . |
| 5,094,255 | 3/1992 | Ringle ........................ 132/321 |
| 5,098,711 | 3/1992 | Hill et al. ..................... 132/231 |
| 5,125,834 | 6/1992 | Swan . |
| 5,226,434 | 7/1993 | Britton et al. ............... 132/329 |
| 5,300,290 | 4/1994 | Spencer ....................... 132/321 |
| 5,312,248 | 5/1994 | Zandkarimi . |
| 5,326,261 | 7/1994 | Rains . |
| 5,353,820 | 10/1994 | Suhonen et al. ............. 132/321 |
| 5,357,989 | 10/1994 | Gathani . |
| 5,395,239 | 3/1995 | Komatsu et al. . |
| 5,423,337 | 6/1995 | Ahlert et al. ................. 132/321 |
| 5,433,226 | 7/1995 | Burch .......................... 132/321 |
| 5,458,487 | 10/1995 | Komatsu et al. . |
| 5,474,967 | 12/1995 | Komatsu et al. . |

FOREIGN PATENT DOCUMENTS 2 066 074   12/1979   United Kingdom .

*Primary Examiner*—Todd E. Manahan
*Assistant Examiner*—E. Robert
*Attorney, Agent, or Firm*—Brinks Hofer Gilson & Lione

[57] ABSTRACT

Dental floss impregnated with a pressure sensitive dye for marking teeth. The pressure sensitive dye is released in response to the application of interproximal pressure when the dental floss is inserted between a tooth and an adjacent tooth having an interproximal spacing less than the diameter of the dental floss. The pressure sensitive dye produces a localized stained area at locations of interproximal tooth contact between the two teeth so that the dentist points of contact between crowns, bridges and natural teeth.

9 Claims, No Drawings

DENTAL FLOSS WITH A PRESSURE SENSITIVE MATERIAL

BACKGROUND OF THE INVENTION

1. Field of the Invention

The invention relates generally to dentistry, and in particular, to dental floss impregnated or coated with a pressure sensitive material for marking teeth.

2. Related Art

When dentists seat crowns and bridges, interproximal contacts are just as important as occlusal or biting contacts. At present, only articulating paper is being used to determine interproximal contacts. However, articulating paper is generally too thick and bulky for determining interproximal contacts. Using articulating paper that is too thick leaves marks on the crowns and bridges that are inaccurately large. As a result, the dentist may reduce too much crown structure leading to open contacts, food impaction, periodontal disease and patient dissatisfaction.

To solve the foregoing problems, it is an object of the invention to provide articulating floss impregnated with pressure sensitive material. Articulating floss used in the same situations provides the dentist with very accurate contacts. These contacts, usually within millimeters, give the dentist a much better clinical assessment of where and how much crown material to reduce, thereby leaving correct interproximal contacts.

SUMMARY OF THE INVENTION

It is an object of the invention to provide dental floss for marking tooth contact points interproximally between one tooth and an adjacent tooth.

It is an another object of the invention to provide a means for marking interproximal spacing between teeth is a simple and economical manner.

It is yet another object of the invention to provide a means for precisely measure interproximal contact between one tooth and an adjacent tooth.

To achieve these and other objects of the invention, a dental floss for marking teeth comprises an elongate uninterrupted strand of fiber material having a predetermined diameter and impregnated or coated with a pressure sensitive material. The pressure sensitive material is released from the fiber material in response to interproximal contact when an interproximal distance between one tooth and an adjacent tooth is smaller than the diameter of the dental floss.

These and other aspects and advantages of the invention are described or apparent from the following detailed description of the preferred embodiments.

DETAILED DESCRIPTION OF THE PREFERRED EMBODIMENTS

The dental floss for marking teeth comprises an elongate uninterrupted strand of material, such as a elastomer or acrylic material having a predetermined diameter and impregnated or coated with a pressure sensitive material, such as a dye or chemically interactive material.

The pressure sensitive dye may comprise any one of a variety of substances well known in the art for marking teeth. One example of the pressure sensitive material comprises a plurality of dispersed cells each containing one of two chemically interactive substances as described in U.S. Pat. No. 3,918,160 herein incorporated by reference. The cells are ruptured in response to interproximal pressure caused by the distance between one tooth and an adjacent tooth being smaller than the diameter of the dental floss. The ruptured cells chemically interact and produce localized stained areas at precise locations where the interproximal spacing between the one tooth and the adjacent tooth is less than the diameter of the dental floss. In this manner, the dentist can accurately determine interproximal spacing between the teeth by observing the stained areas on the teeth.

The precise nature of the pressure sensitive material is not critical to the invention. In general, the pressure sensitive material should be selected so as to be non-toxic to the patient in small quantities and to produce a color that is readily distinguishable from the overall color of the teeth.

The dental floss may also be impregnated or coated with the pressure sensitive material by immersing the dental floss in an emulsion containing the pressure sensitive material and then drying the dental floss as described in U.S. Pat. No. 2,299,693 herein incorporated by reference.

In one embodiment, the pressure sensitive material contains two types of profusely dispersed minute liquid-containing cells. The two types of liquid-containing cells are kept chemically insulated from each other until the cells are ruptured by interproximal pressure when the dental floss is inserted between one tooth and an adjacent tooth due to the interproximal spacing between the teeth being smaller than the diameter of the dental floss.

In another embodiment, the pressure sensitive material contains chemically interactive materials, such as Ph indicators as described in U.S. Pat. No. 3,918,160 referenced above. For example, an acid-base indicator, such as phenophthalein may be utilized as one of the interactive materials and the other material may be sodium-tetraborate.

In another embodiment, the pressure sensitive material may comprise a plurality of micro-capsules dispersed in a carrier of a type well known in the art. The term "micro-capsule" designates the class of materials wherein a nucleus or microscopic drop of liquid material is surrounded by a mantle of relatively impervious material. The mantle is relatively thin and pressure sensitive so as to be ruptured easily when pressure is applied.

In view of the foregoing, it can be appreciated that the invention is not limited by the chemically interactive material used to indicate the stained areas on the teeth and that the invention can be practiced with any pressure sensitive material that is non-toxic to the patient and produces a color that is readily distinguishable from the overall color of the teeth.

It should also be appreciated that the diameter of the dental floss according to the invention can be of different predetermined diametral thickness depending on the interproximal spacing between the teeth to be indicated by the pressure sensitive material. In the preferred embodiment, the dental floss has a substantially uniform cross sectional area of a circular shape. Typically, the diameter of the dental floss may be between approximately 0.25 and 10 mils thickness.

While this invention has been described in conjunction with specific embodiments, it is evident that many alternatives, modifications and variations will be apparent to those skilled in the art. Accordingly, the preferred embodiments of the invention as set forth herein are intended to be illustrative, rather than limiting. Various changes may be made without departing from the spirit and scope of the invention as defined in the following claims.

What is claimed is:

1. Dental floss for marking teeth, comprising:

an elongate uninterrupted strand of fiber material having a predetermined diameter and impregnated with a pressure sensitive material having a plurality of chemically interactive substances, wherein cells of said pressure sensitive material are ruptured and chemically interact with each other to produce localized stained areas at locations of interproximal contact when said fiber material is inserted between one tooth and an adjacent tooth and an interproximal distance between the two teeth is smaller than the diameter of said fiber material.

2. The dental floss according to claim 1, wherein said pressure sensitive material comprises two types of profusely dispersed minute liquid-containing cells.

3. The dental floss according to claim 1, wherein said pressure sensitive material comprises a plurality of microcapsules dispersed in a carrier.

4. The dental floss according to claim 1, wherein said fiber material has a diameter of between approximately 0.25 and 10 mils.

5. The dental floss according to claim 1, wherein said fiber material comprises acrylic material.

6. The dental floss according to claim 1, wherein said fiber material comprises elastomeric material.

7. Dental floss for marking teeth, comprising:

an elongate uninterrupted strand of fiber material impregnated with a pressure sensitive material having two chemically interactive substances, said fiber material having a substantially uniform cross-sectional area along its length, wherein said pressure sensitive material is released from said fiber material when said fiber material is inserted between on tooth and an adjacent tooth and an interproximal space between the two teeth is smaller than the cross-sectional area of said fiber material, thereby-rupturing cells of the two chemically interactive substances and producing a localized stain area indicating interproximal contact between the two adjacent teeth.

8. An articulating dental floss, comprising:

an elongate uninterrupted strand of fiber material impregnated with a pressure sensitive material having at least two chemically interactive substances, wherein cells of the two chemically interactive substances are ruptured by interproximal pressure caused by one tooth and an adjacent tooth having a spacing smaller than a diameter of said fiber material when said dental floss is inserted between the teeth, thereby producing localized stained areas indicating interproximal contact between the two adjacent teeth.

9. The dental floss according to claim 8, wherein said uninterrupted strand of fiber material has a substantially uniform cross-sectional area along its length.

* * * * *